(12) United States Patent
Albert

(10) Patent No.: US 11,234,604 B2
(45) Date of Patent: Feb. 1, 2022

(54) BLOOD PRESSURE MONITOR

(71) Applicant: AliveCor, Inc.

(72) Inventor: David E. Albert, Oklahoma City, OK (US)

(73) Assignee: AliveCor, Inc., Mountain View, CA (US)

(*) Notice: Subject to any disclaimer, the term of this patent is extended or adjusted under 35 U.S.C. 154(b) by 650 days.

(21) Appl. No.: 16/040,166

(22) Filed: Jul. 19, 2018

(65) Prior Publication Data
US 2018/0317784 A1    Nov. 8, 2018

Related U.S. Application Data

(63) Continuation of application No. 14/705,755, filed on May 6, 2015, now Pat. No. 10,028,668.
(Continued)

(51) Int. Cl.
A61B 5/024    (2006.01)
A61B 5/021    (2006.01)
(Continued)

(52) U.S. Cl.
CPC ...... *A61B 5/02416* (2013.01); *A61B 5/02125* (2013.01); *A61B 5/318* (2021.01); *A61B 5/332* (2021.01); *A61B 5/681* (2013.01); *A61B 5/6898* (2013.01); *A61B 5/7278* (2013.01); *A61B 5/742* (2013.01); *A61B 2505/07* (2013.01)

(58) Field of Classification Search
None
See application file for complete search history.

(56) References Cited

U.S. PATENT DOCUMENTS 6,038,469 A    3/2000  Karlsson et al.
7,674,231 B2*  3/2010  McCombie ........ A61B 5/02125
                                              600/485
(Continued)

FOREIGN PATENT DOCUMENTS

WO    2013009589 A1    1/2013
WO    2014022906 A1    2/2014
(Continued)

OTHER PUBLICATIONS

PCT/US2015/029469 International Preliminary Report on Patentability dated Nov. 17, 2016.
(Continued)

*Primary Examiner* — Yi-Shan Yang
(74) *Attorney, Agent, or Firm* — Womble Bond Dickinson (US) LLP

(57) ABSTRACT

Described herein are methods, systems, and software for monitoring blood pressure. In some embodiments, a using a mobile device is used. The blood pressure monitoring system utilizes heart rate measurements at two separate locations on the body to calculate a differential pulse arrival time which is used to estimate blood pressure. The heart rate measurements can be taken simultaneously, or they can be taken sequentially while simultaneously taking ECG measurement. If taken sequentially, the heart rate measurements are aligned with the ECG to determine the differential. Accurate, inexpensive, and discreet blood pressure monitoring is thus provided.

22 Claims, 7 Drawing Sheets

Related U.S. Application Data

(60) Provisional application No. 61/989,279, filed on May 6, 2014.

(51) Int. Cl.
*A61B 5/00* (2006.01)
*A61B 5/318* (2021.01)
*A61B 5/332* (2021.01)

(56) References Cited

U.S. PATENT DOCUMENTS

| | | |
|---|---|---|
| 8,301,232 B2 | 10/2012 | Albert et al. |
| 9,554,748 B2 | 1/2017 | Banet et al. |
| 2004/0260184 A1* | 12/2004 | Narimatsu ............ A61B 5/021 |
| | | 600/481 |
| 2006/0074322 A1 | 4/2006 | Nitzan |
| 2008/0194978 A1 | 8/2008 | Beker et al. |
| 2009/0318820 A1 | 12/2009 | Toledo et al. |
| 2013/0245456 A1 | 9/2013 | Ferguson et al. |
| 2014/0031646 A1 | 1/2014 | Yakirevich et al. |
| 2014/0043457 A1* | 2/2014 | Stergiou ............ A61B 5/02125 |
| | | 348/77 |
| 2014/0051941 A1* | 2/2014 | Messerschmidt .. A61B 5/02416 |
| | | 600/301 |
| 2014/0073969 A1* | 3/2014 | Zou ...................... A61B 5/0205 |
| | | 600/479 |
| 2014/0107493 A1 | 4/2014 | Yuen et al. |
| 2014/0249398 A1 | 9/2014 | Morris et al. |
| 2015/0073239 A1 | 3/2015 | Pei et al. |
| 2017/0202463 A1* | 7/2017 | Muhlsteff ............ A61B 5/0002 |

FOREIGN PATENT DOCUMENTS

| | | |
|---|---|---|
| WO | 2014028736 A1 | 2/2014 |
| WO | 2014036436 A1 | 3/2014 |

OTHER PUBLICATIONS

PCT/US2015/029469 International Search Report and Written Opinion dated Aug. 7, 2015.

* cited by examiner

Measurement 1 at point A

Measurement 2 at point B

Time aligned measurements 1 and 2

Differential PTT = PTT2−PTT1

BLOOD PRESSURE MONITOR

CROSS-REFERENCE

This application claims the benefit of U.S. application Ser. No. 14/705,755, filed May 6, 2015, and U.S. Provisional Application No. 61/989,279, filed May 6, 2014, which are incorporated herein by reference.

INCORPORATED BY REFERENCE STATEMENT

All publications, patents, and patent applications mentioned in this specification are herein incorporated by reference to the same extent as if each individual publication, patent, or patent application was specifically and individually indicated to be incorporated by reference.

U.S. Ser. No. 13/420,520, filed Mar. 14, 2012, now U.S. Pat. No. 8,301,232, is hereby expressly incorporated herein by reference in its entirety.

BACKGROUND

Blood pressure is a key vital sign monitored by physicians, it is used for the diagnosis of many medical conditions, and by itself is monitored as a key metric for the management of disease. The standard measure of blood pressure is the auscultatory method, wherein a specialist inflates a cuff around the arm and uses a stethoscope to determine the systolic blood pressure and the diastolic blood pressure. Hypertension, an elevation in either the systolic or diastolic blood pressure, is a medical condition that afflicts some 70 million Americans, and it is estimated that only about half of these people have their disease under control.

SUMMARY

The presently claimed and disclosed concepts relate generally to heart monitoring devices and methods and, more particularly, but not by way of limitation, to methods, devices, systems and software for measuring blood pressure using a mobile device. The methods described in this disclosure are in stark contrast to standard blood pressure methods. The method requires the use of a cuff, which is bulky, costly, and does not allow continuous monitoring. There is an unmet need for blood pressure monitoring, especially in personal healthcare applications. Compared to standard methods of blood pressure monitoring, the methods of the disclosure provide advantages with regard to cost, convenience, and the ability to intermittently or continuously monitor blood pressure for the management of disease or for research purposes.

Disclosed herein, is a method for non-invasive determination of a blood pressure in a subject, said method comprising; providing to a subject a mobile computing device comprising a first and a second electrode and an optical sensor, wherein said first and second electrodes are configured to sense an electrocardiogram, wherein said optical sensor is configured to sense a photoplethysmogram, wherein a software application is configured to determine a differential pulse arrival time using input from said first and second electrodes and said optical sensor, and display a blood pressure reading of said subject based on the differential pulse arrival time. In certain embodiments, said mobile computing device comprises a smartphone. In certain embodiments, said mobile computing device comprises a tablet. In certain embodiments, said mobile computing device comprises a smart watch. In certain embodiments, said optical sensor is a camera that operates at a minimum of 30 frames per second. In certain embodiments, said first and second electrodes are removable from said mobile computing device.

Disclosed herein is a method for non-invasive determination of a blood pressure in a subject, said method comprising; providing to the subject a software application configured for use with a mobile computing device, wherein said mobile computing device comprises a first and a second electrode and an optical sensor, wherein said first and said second electrodes are configured to sense an electrocardiogram, wherein said optical sensor is configured to sense a photoplethysmogram, wherein said software application is configured to determine a differential pulse arrival time using input from said first and second electrodes and said optical sensor, and display a blood pressure reading of said subject based on the differential pulse arrival time. In certain embodiments, said mobile computing device comprises a smartphone. In certain embodiments, said mobile computing device comprises a tablet. In certain embodiments, said mobile computing device comprises a smartwatch. In certain embodiments, said optical sensor is a camera that operates at a minimum of 30 frames per second. In certain embodiments, said first and second electrodes are removable from said mobile computing device.

Also disclosed herein, is method for non-invasive determination of a blood pressure in a subject, said method comprising; engaging, by said subject, a first electrode on a mobile computing device with a first skin surface, and a second electrode on said mobile computing device with a second skin surface such that a first and a second electrocardiogram is sensed; engaging, by said subject, simultaneously to engaging said first and said second electrodes, an optical sensor on said mobile computing device such that a first and a second photoplethysmogram is sensed from different body locations; and wherein said mobile computing device includes software configured to generate an average electrocardiogram from said first and said second electrocardiograms, wherein said software is configured to determine a differential pulse arrival time based on said average electrocardiogram and said first and said second photoplethysmograms, and wherein said software is configured to determine said blood pressure of said subject based on said differential pulse arrivalion time. In an embodiment, said software application is configured to communicate with a network server. In certain embodiments, said mobile computing device comprises a smartphone. In certain embodiments, said mobile computing device comprises a tablet. In certain embodiments, said mobile computing device comprises a smartwatch.

Also disclosed herein, is a system for non-invasive determination of a blood pressure in a subject, comprising; a mobile computing device comprising a processor, an optical sensor, and a display; a first and a second electrode attached to said mobile computing device, coupled to said processor; and a non-transitory computer readable storage medium encoded with a computer program including instructions executable by said processor to cause said processor to; receive a first electrocardiogram from said first and second electrodes and receive at the same time a first photoplethysmogram from said optical sensor; receive a second electrocardiogram from said first and second electrodes and receive at the second time a second photoplethysmogram from said optical sensor; generate an average electrocardiogram from said first and second electrocardiograms; determine a differential pulse arrival time based on said average electrocardiogram and said first and second photoplethysmograms; and determine said blood pressure of said subject based on said differential pulse arrival time. In certain embodiments, said software application is configured to communicate with a network server. In certain embodiments, said mobile computing device comprises a smartphone. In certain embodiments, said mobile computing device comprises a tablet. In certain embodiments, said mobile computing device comprises a smart watch. In certain embodiments, said optical sensor is a camera that operates at a minimum of 30 frames per second. In certain embodiments, said optical sensor is a camera that operates at a minimum of 60 frames per second. In certain embodiments, said first and second electrodes are removable from said mobile computing device. In certain embodiments, the system further comprises a dedicated means to initiate the steps of the system.

Also described herein is a method for the non-invasive determination of blood pressure in a subject, the method comprising using a first optical sensor to detect a pulse in the subject at a first location of the subjects body using a second optical sensor to detect a pulse in the subject at a second location of the subjects body at the same time; and calculating the blood pressure of the subject using a non-transitory computer readable storage media with a computer program configured to calculate a differential pulse arrival time between the first location and the second location; wherein the method does not utilize a blood pressure cuff or acoustic device to sense a subjects pulse. In an embodiment, the first location is a finger of the subject. In an embodiment, the second location is the subjects face. In an embodiment, the method utilizes a mobile phone. In an embodiment, the method utilizes a tablet computer. In an embodiment, the method utilizes a smart watch. In an embodiment, at least one of the optical sensors is a camera. In an embodiment, the camera has a speed of 30 frames per second or greater. In an embodiment, the camera has a speed of 60 frames per second or greater. In an embodiment, the output of the computer program is sent to a network server.

Also described herein is a method for the non-invasive determination of blood pressure in a subject, the method comprising: using electrodes to detect the ECG of a subject; (a) using an optical sensor or camera to detect a pulse in the subject at a first location of the subjects body; (b) repeating steps (a) and (b) at a second location of the subjects body; and (c) calculating the blood pressure of the subject using a non-transitory computer readable storage media with a computer program configured to calculate a pulse arrival time; wherein the method does not utilize a blood pressure cuff or acoustic device to sense a subjects pulse. In an embodiment, the electrodes detect a QRS complex at the hands of the subject. In an embodiment, at either the first or second location that optical sensor detects is the subjects face. In an embodiment, the method utilizes a mobile phone. In an embodiment, the method utilizes a tablet computer. In an embodiment, the method utilizes a smart watch. In an embodiment, the optical sensors is a camera or cameras. In an embodiment, the camera or cameras have a speed of 30 frames per second or greater. In an embodiment, the camera or cameras have a speed of 60 frames per second or greater. In an embodiment, the output of the computer program is sent to a network server.

BRIEF DESCRIPTION OF THE DRAWINGS

The novel features of the described subject matter are set forth with particularity in the appended claims. A better understanding of the features and advantages of the presently described subject matter will be obtained by reference to the following detailed description that sets forth illustrative embodiments, in which the principles of the described subject matter are utilized, and the accompanying drawings of which:

DETAILED DESCRIPTION

Figure 1:
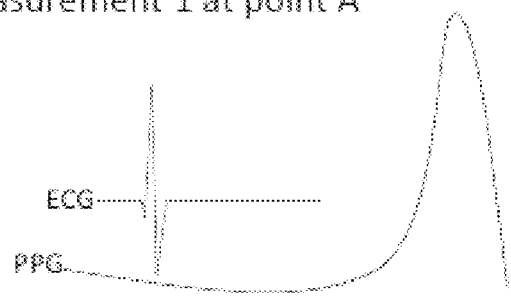
FIG. 1 shows a simplified schema for time alignment of PPG measurements.
Figure 1:
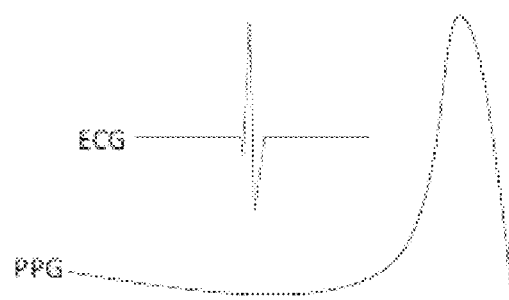
Figure 1:
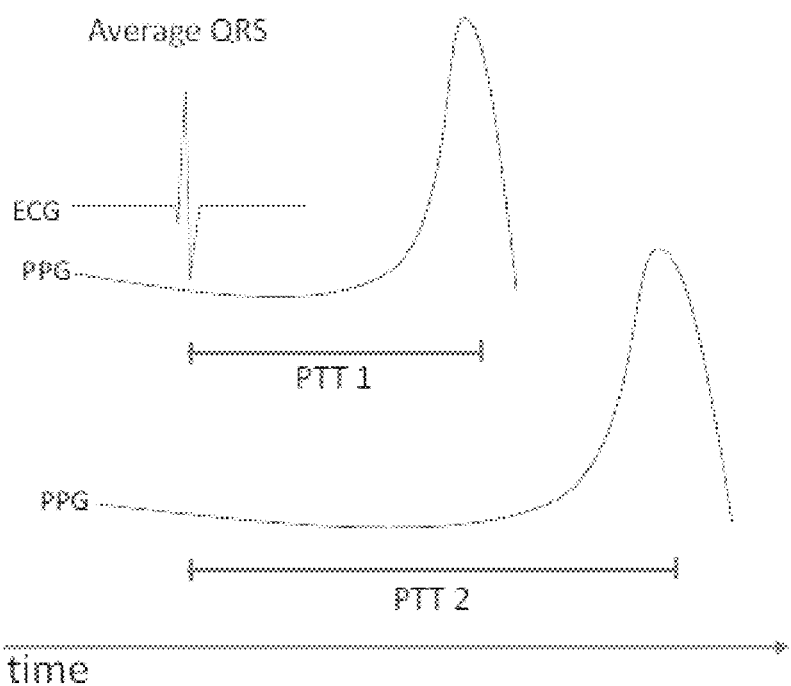
Figure 2:
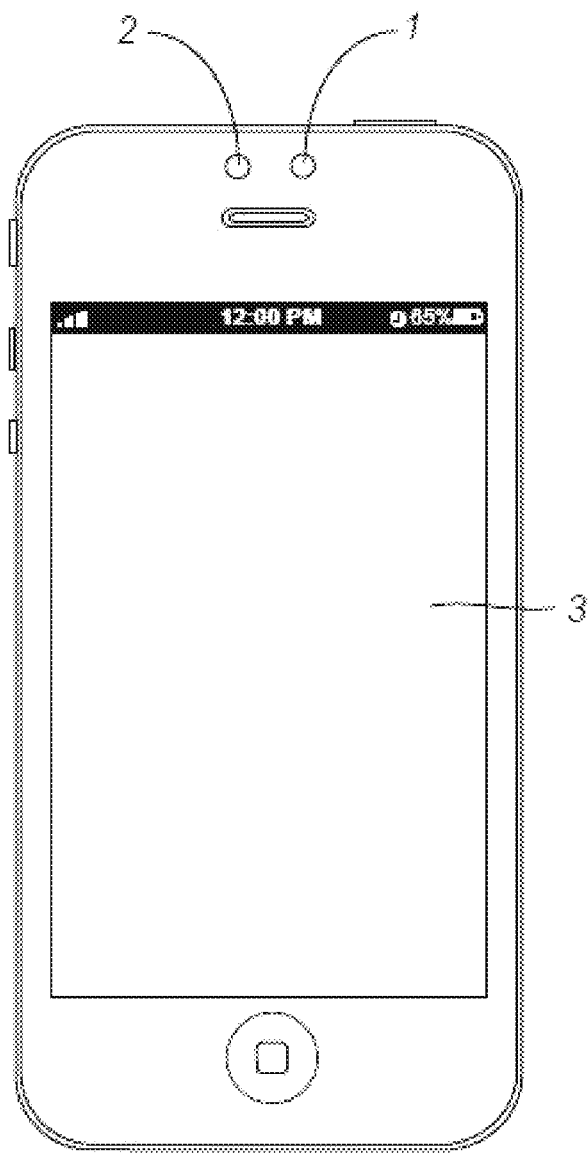
FIG. 2 shows a non-limiting example of a person using a mobile device to determine their blood pressure.
Figure 3:
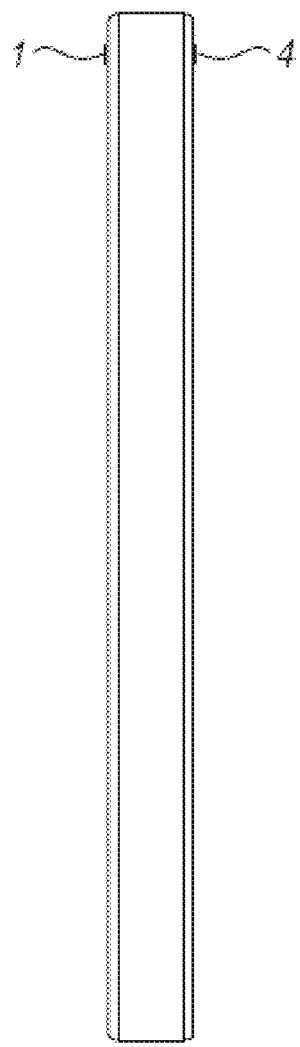
FIG. 3 shows a non-limiting example of a finger placed over a rear facing camera of a mobile phone for a photoplethysmogram (PPG) measurement.
Figure 4:
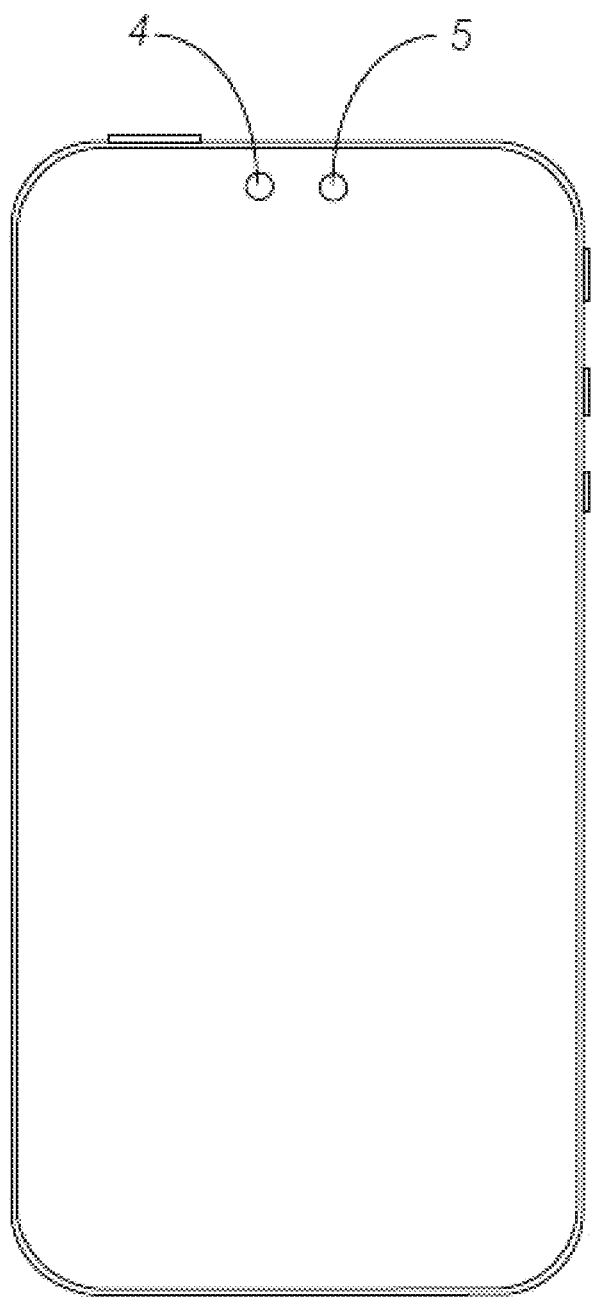
FIG. 4 shows hand placement on a device equipped with electrodes for measuring a QRS complex.

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Certain Definitions

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

While the term "extremities" is used herein for the body area used to detect heart rate, it need not be an extremity and could be, for example, a chest or stomach location on the body. In general, using a position close to the heart and comparing to a position far from the heart will provide the longest differential and therefore increased accuracy.

A "subject" as defined by this disclosure can be any human person in which blood pressure monitoring would be advantageous. The person can have a diagnosed illness, including but not limited to, primary hypertension, secondary hypertension, or gestational hypertension. The person can be considered healthy and undiagnosed with any disease. The methods of this disclosure include monitoring of both healthy persons and those diagnosed with a medical condition.

Non-Invasive Blood Pressure Measurements

Pressure waves produced at the heart propagate through the arteries at a certain velocity known as the pulse wave velocity (PWV). The PWV depends on the blood pressure and the elastic properties of arteries. A person's blood pressure has been shown to be proportional to, or a function of, the pressure wave velocity. The PWV is equal to the length of a vessel (l) divided by the time it takes for a pressure pulse to arrival through a vessel. The time it takes for a pressure pulse to travel the length of the vessel (l) is known as the pulse arrival time (PTT), or pulse arrival time (PAT). PTT and PAT are used interchangeably herein. The formula for determination of the PWV is as follows:

$$PWV = l/PTT$$

The PAT is considered to have a correlation with blood pressure, and attempts have been made to use the PAT for indirect blood pressure measurements.

It was once thought that the PAT could be estimated as the time between the QRS peak on an ECG and the time the wave or pulse of blood reaches an extremity. The QRS peak could be measured using known ECG devices, and the time the pulse of blood reaches an extremity could be measured using known methods such as photoplethysmogram (PPG). The PPG method detects changes in blood volume during a cardiac cycle by illuminating the skin, and measuring changes in light absorption. PPG has become a popular method for measuring heart rate and oxygen saturation by using, for example, a mobile phone's embedded flash as a light source and the camera as a light sensor when held adjacent a peripheral site such as the finger. The PPG measurement can also be made at another peripheral site such as the ear, forehead, or chest. The PPG signal obtained consists of pulses that reflect the change in vascular blood volume with each cardiac beat.

Such time measurements used for the PWV included a "pre-ejection" period, which is the time interval from the beginning of electrical stimulation of the ventricles to the actual opening of the aortic valve. The aortic valve will not open until the blood pressure within the ventricle is greater than the pressure in the aorta. Thus, present attempts to measure PWV actually use a length of artery divided by the sum of the pre-ejection period plus the time for the pulse to travel that length of artery.

By making simultaneous PPG measurements at different locations of the body, the effect of the pre-ejection period can be eliminated by subtraction. PPG measurements can be made by a mobile device equipped with a camera. Key to eliminating the effect of the pre-ejection period is calculating a differential PAT, i.e. the difference between when the pulse reaches extremity A and when it reaches extremity B. This eliminates the pre ejection period, because it is the same for both extremities, and is removed by using the differential PAT ($PAT_A - PAT_B$). The differential PAT time can be measured, for example, by using a mobile phone having both front and back cameras, and thus perform PPG measurements simultaneously at two different locations of the body. By using the differential PAT one can calculate a PWV using the following equation:

$$PWV = (I_A - I_B)/(PTT_A - PTT_B)$$

Where $I_A$ corresponds to the distance from the heart to extremity A and $I_B$ corresponds to the distance from the heart to extremity B. If repeated measurements are made at the same body locations over time, then ($I_A - I_B$) need not be determined. Since blood pressure is proportional to the PWV, and the PWV is inversely proportional to the differential PAT, blood pressure can be determined by calculating the differential PAT. If the PAT can be correlated to blood pressure by an independent method, for example, the auscultatory method or an automated oscillometric blood pressure device at home one can track changes in blood pressure, merely by tracking changes in PAT.

Alternatively a differential PAT can be calculated using two successive, not simultaneous, PPG measurements, if an ECG is also employed to synchronize the PPG measurements. If successive ECG measurements and their corresponding PPG measurements are made, they can be time aligned by averaging the QRS readings from the ECGs associated with each PPG measurement, and then aligning the PPG measurements taken to the average QRS. This will result in two PATs derived from average QRS complexes. The differential PAT is the difference between these two PATs. A schematic of this process is shown in FIG. 1. In this way the effect of the pre-ejection period can be minimized. As with the previous method the differential PAT can be correlated to blood pressure by an independent method, for example, the auscultatory method or an automated oscillometric blood pressure device at home allowing one to track changes in blood pressure, merely by tracking changes in the differential PAT.

By occasionally calibrating an individual's PAT to a given blood pressure as measured by, for example, the auscultatory method or an automated oscillometric device at home, one can calibrate the differential PAT with blood pressure. As a result one can utilize a mobile device throughout the day to track their blood pressure when other methods may not be convenient. In certain embodiments, the method described herein requires calibration once a day. In certain embodiments, the method described herein requires calibration every other day. In certain embodiments, the method described herein requires calibration 2, 3, 4, or 5 times a week. In certain embodiments, the method described herein requires calibration once a week. In certain embodiments, the calibration is adaptive, whereby multiple calibration events are stored and used to improve the overall accuracy of the method.

Certain Embodiments of the Disclosure

Disclosed herein is a method for non-invasive determination of a blood pressure in a subject, said method comprising: providing to a subject a mobile computing device comprising a first and a second electrode and an optical sensor, wherein said first and second electrodes are configured to sense an electrocardiogram, wherein said optical sensor is configured to sense a photoplethysmogram, wherein a software application is configured to determine a differential pulse arrival time using input from said first and second electrodes and said optical sensor, and display a blood pressure reading of said subject based on the differential pulse arrival time.

Non limiting embodiments of exemplar mobile computing devices that can execute the methods of this disclosure are shown in FIGS. 2-5. In certain embodiments, the mobile computing device is a mobile phone. In certain embodiments, the mobile computing device is a smart phone. In certain embodiments, the mobile computing device is a tablet computer. In certain embodiments, the mobile computing device is a smart watch. In certain embodiments, the mobile computing device is a portable laptop computer. In certain embodiments, the mobile computing device is a dedicated device for measuring vital signs. In certain embodiments, the mobile computing device is a dedicated device for measuring blood pressure.

In certain embodiments, the mobile computing device communicates with a network server. In certain embodiments, the mobile computing device communicates with a network server by Wi-Fi. In certain embodiments, the mobile computing device communicates with a network server using a cellular network. In certain embodiments, the mobile computing device communicates with another computer wirelessly. In certain embodiments, the mobile computing device communicates with another computer by Bluetooth™. In certain embodiments, the mobile computing device communicates with another computer by a wired connection.

In certain embodiments, the mobile device has a single optical sensor. In certain embodiments, the mobile computing device has two optical sensors. In certain embodiments, the mobile computing device has three optical sensors. In certain embodiments any or all of the optical sensors is a camera. In certain embodiments, any or all of the cameras operate with a speed of equal to or greater than 30 frames per second. In certain embodiments, any or all of the cameras operate with a speed of equal to or greater than 60 frames per second. In certain embodiments, any or all of the cameras operate with a speed of equal to or greater than 120 frames per second. In certain embodiments each optical sensor is paired with a means of illumination. The means of illumination could be an LED.

In certain embodiments, the mobile computing device has an optical sensor that is a forward-facing camera 1, which can be positioned anywhere on the device that allows an unobstructed view of the subject or a location on the subjects body while being held. In certain embodiments the camera can be configured to operate as a PPG. In certain embodiments, the camera speed is equal to or greater than 30 frames per second. In certain embodiments, the camera speed is equal to or greater than 60 frames per second. In certain embodiments, the camera speed is equal to or greater than 120 frames per second. In certain embodiments, the camera uses a charge couple device (CCD) sensor. In certain embodiments, the camera uses complementary metal oxide semiconductor (CMOS) sensor. In certain embodiments the camera has a resolution of 1, 2, 3, 4, 5, 6, 7, 8, 9, 10, 11, 12, 13, 14, 15, 16, 17, 18, 19, 20 megapixels or more. In certain embodiments, the device also contains a source of illumination 2 which can be used to aid the camera in detecting and imaging a location of the subjects body, and in PPG measurements. In certain embodiments, the source of illumination is an LED. In certain embodiments, the LED can be illuminated continuously or intermittently.

In certain embodiments, the mobile computing device has an optical sensor that is a rear-facing camera 4, which can be positioned anywhere on the device that allows an unobstructed view of the subject or a location on the subjects body while being held. In certain embodiments the camera can be configured to operate as a PPG. In certain embodiments, the camera speed is equal to or greater than 30 frames per second. In certain embodiments, the camera speed is equal to or greater than 60 frames per second. In certain embodiments, the camera speed is equal to or greater than 120 frames per second. In certain embodiments, the camera uses a charge couple device (CCD) sensor. In certain embodiments, the camera uses complementary metal oxide semiconductor (CMOS) sensor. In certain embodiments the camera has a resolution of 1, 2, 3, 4, 5, 6, 7, 8, 9, 10, 11, 12, 13, 14, 15, 16, 17, 18, 19, 20 megapixels or more. In certain embodiments, the device also contains a source of illumination 5 which can be used to aid the camera in detecting and imaging a location of the subjects body, and in PPG measurements. In certain embodiments, the source of illumination is an LED. In certain embodiments, the LED can be illuminated continuously or intermittently.

In certain embodiments, the mobile computing device has a display 3 which can be utilized as a graphical user interface. In certain embodiments, the display can be touch sensitive. The device can receive instructions and parameters from the user via the display 3. The display can communicate instructions to the user, aid in positioning of at least one camera, and display results of the monitoring. In some embodiments, the device may be controlled by voice commands. In some embodiments the device may be controlled remotely.

Figure 5:
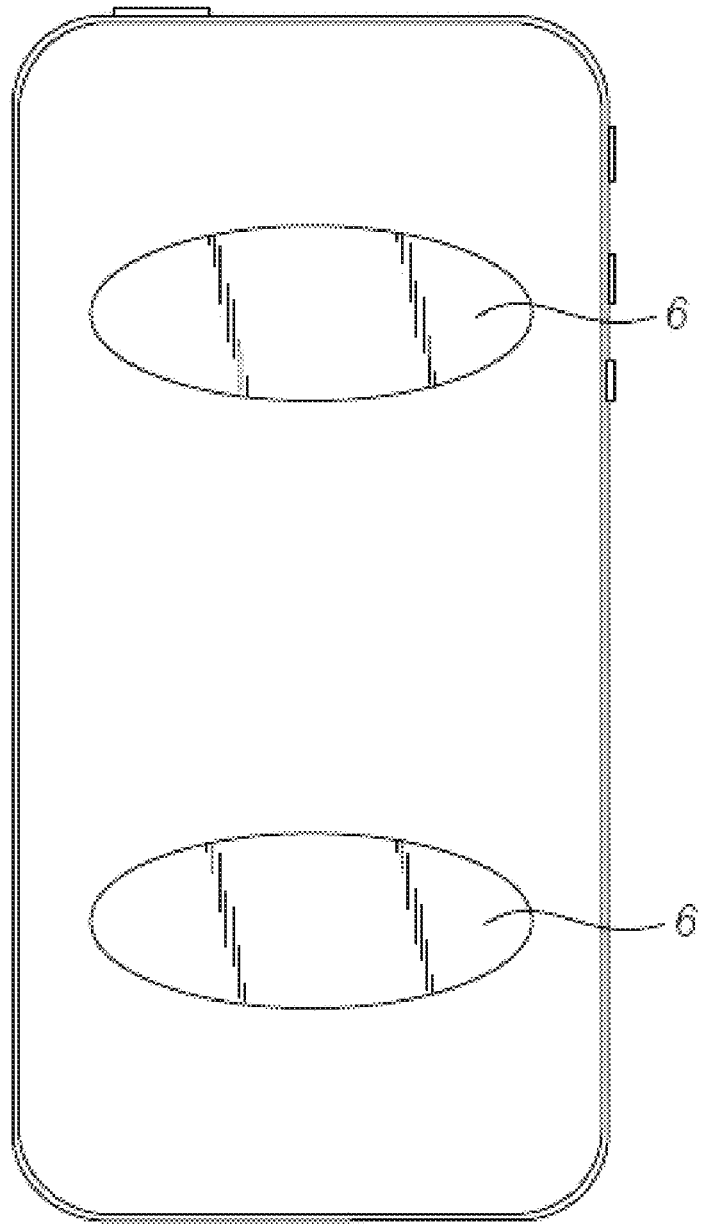
FIG. 5 shows a front view of a device which can implement the methods of this disclosure.

A non-limiting embodiment of a mobile computing device that can be configured to measure a subjects blood pressure using ECG measurements is shown in FIG. 5. The device can have dual electrodes 6 to measure an electrical potential difference used to calculate a heartbeat. In certain embodiments, the electrodes are integrated into the device. In certain embodiments, the electrodes are separate from the device in the form of a removable cover. In certain embodiments the electrodes are on the back of the device. In certain embodiments, the electrodes are on the sides of the device. In certain embodiments, the electrodes are on the front of the device. In certain embodiments, the electrodes are ergonomically shaped.

In certain embodiments, the mobile computing device may have a means dedicated to initiating the method of measuring blood pressure described herein. In certain embodiments, the means may be a button, switch, toggle switch, capacitive interface, voice command, remote command or the like. In certain embodiments, the mobile computing device may provide auditory feed-back. In certain embodiments, the auditory feedback may guide the user for proper use of the device, alert the user as to when the device is being used incorrectly, alert the user as to when measurements are being made, alert the user as to the outcome of measurements, alert the user for a need to calibrate or otherwise service the device.

In certain embodiments, any part of the body can utilized to make PPG measurements. In certain embodiments, a finger can utilized to make PPG measurements. In certain embodiments, the face can utilized to make PPG measurements. In certain embodiments, an ear can utilized to make PPG measurements. In certain embodiments, the chest can utilized to make PPG measurements. In certain embodiments, the stomach can utilized to make PPG measurements. In certain embodiments, the neck can utilized to make PPG measurements.

Also disclosed herein is a method for non-invasive determination of a blood pressure in a subject, said method comprising: providing to the subject a software application configured for use with a mobile computing device, wherein said mobile computing device comprises a first and a second electrode and an optical sensor, wherein said first and said second electrodes are configured to sense an electrocardiogram, wherein said optical sensor is configured to sense a photoplethysmogram, wherein said software application is configured to determine a differential pulse arrival time using input from said first and second electrodes and said optical sensor, and display a blood pressure reading of said subject based on the differential pulse arrival time.

In certain embodiments, the software application controls the optical sensor. In certain embodiments, the software application controls the first and second electrodes. In certain embodiments, the software application calculates a differential PAT. In certain embodiments, the software application correlates a differential PAT with a blood pressure using calibration data. In certain embodiments, the software application calculates an average QRS from two or more ECG readings. In certain embodiments, the software application calculates an average QRS from 3, 4, 5, 6, 7, 8, 9, 10 or more ECG readings. In certain embodiments, the software application calculates an average QRS from 10, 20, 30, 40, 50, 6, 70, 80, 90, 100 or more ECG readings. In certain embodiments, the software application correlates a differential PAT with a blood pressure using calibration data. In certain embodiments, the software application correlates a differential PAT with a blood pressure using calibration data. In certain embodiments, the software can be configured for multiple users. In certain embodiments the software stores individual differential PAT data points. In certain embodiments the software stores individual differential PAT data points that are tagged with meta-data such as time of day, date, geolocation and user.

Software downloadable to a mobile computing device can correlate an individual's blood pressure and differential PAT. An individual owning such a mobile computing device can, for example, measure their blood pressure using a standard cuff-type blood pressure monitor in the morning and then measure their differential PAT to calibrate the correlation between blood pressure and differential PAT. The rest of the day, they can quickly and inconspicuously monitor their blood pressure by merely measuring the differential PAT with their mobile computing device. In certain embodiments, the software application described herein requires calibration once a day. In certain embodiments, the software application described herein requires calibration every other day. In certain embodiments, the software application described herein requires calibration 2, 3, 4, or 5 times a week. In certain embodiments, the software application described herein requires calibration once a week. In certain embodiments, the calibration is adaptive, whereby multiple calibration events are stored and used to improve the overall accuracy of the software.

The software application can allow for the input of biometric data such as height, weight, arm length, leg length, waist circumference, gender, age birthdate and the like. The software uploaded to the mobile device can provide management tools to the user. The tools can include storing blood pressure readings calculating daily, weekly or monthly averages. The stored blood pressure readings can be used to generate a report for use by the subject, a physician, or for a clinical or investigational trial. The report can be sent to health management and tracking software, an e-mail address, a secure server or a social network. The software can be configured to send alerts via e-mail, text message, or social media. The software can also interface with a wearable fitness device such as a Fitbit™, in order to correlate blood pressure with pulse rate, body temperature, sleep-wake cycles, circadian rhythms, movement or any other vital sign or biometric data of interest to the user, a physician, or a clinical or investigational trial.

Disclosed herein is a system for non-invasive determination of a blood pressure in a subject, comprising; a mobile computing device comprising a processor, an optical sensor, and a display; a first and a second electrode attached to said mobile computing device, coupled to said processor; and a non-arrivalory computer readable storage medium encoded with a computer program including instructions executable by said processor to cause said processor to: receive a first electrocardiogram from said first and second electrodes and receive at the same time a first photoplethysmogram from said optical sensor; receive a second electrocardiogram from said first and second electrodes and receive at the same time a second photoplethysmogram from said optical sensor; generate an average electrocardiogram from said first and second electrocardiograms; determine a differential pulse arrival time based on said average electrocardiogram and said first and second photoplethysmograms; and determine said blood pressure of said subject based on said differential pulse arrival time.

Herein are presented various non limiting practical examples of the systems, methods and devices of this disclosure.

Figure 6:
FIG. 6 shows a side view of a device which can implement the methods of this disclosure.
Figure 7:
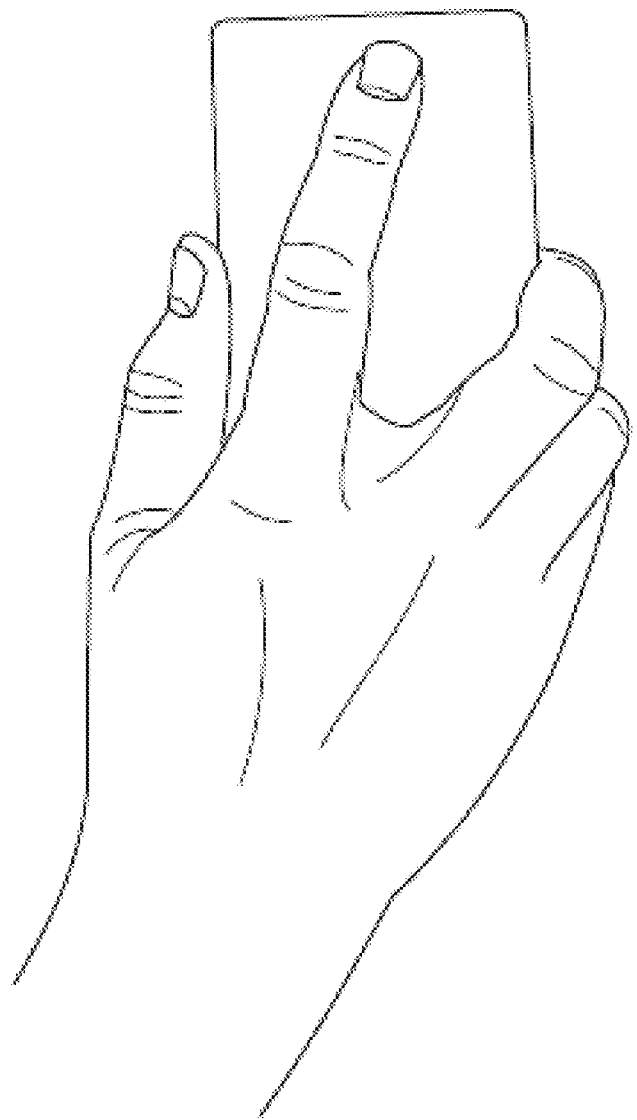
FIG. 7 shows a rear view of a device which can implement the methods of this disclosure.

Example 1—Measurement of Blood Pressure in an Individual Using Dual Optical Sensors A non-limiting example of one embodiment of the method requires holding a mobile phone in front of one's face as shown in FIG. 6, detecting the pulse on a finger covering the camera lens on the back of the mobile phone as shown in FIG. 7, and simultaneously detecting the pulse on one's face using the camera on the front of the mobile phone, the time lag between the finger pulse and the face pulse can be calculated as the differential PAT, and eliminates the pre-ejection period and errors caused by inclusion of the pre-ejection period. The mobile phone can be held at any distance from the face that allows for proper imaging. In certain embodiments, the phone is held less than 3 feet from the face. In certain embodiments, the phone is held less than 2 feet from the face. In certain embodiments, the phone is held less than 1 foot from the face. In certain embodiments, the phone is held less than 6 inches from the face. In certain embodiments, the phone can be used to detect the pulse at a location of the body other than the face, this location can be the neck, chest, stomach or any other location suitable for detecting a pulse. In certain embodiments the methods of this disclosure can be carried out using a tablet computer. In certain embodiments the methods of this disclosure can be carried out using a smart watch. In certain embodiments the methods of this disclosure can be carried out using a device that is solely intended to monitor vital signs.

In a second non-limiting embodiment of this method, a subject can hold a first finger over the forward facing camera, and a second finger over the rear-facing camera of a mobile device. PPG measurements can then be made, and the differential PAT calculated. Using the differential PAT blood pressure can be calculated in a way similar to the first embodiment.

Example 2—Measurement of Blood Pressure in an Individual Using a Single Optical Sensor and an ECG Some individuals may not have a mobile device with front and back camera ability or the frames per second or resolution of the available front camera may not be sufficient to provide accurate blood pressure correlations. However, by using a mobile device enabled to take ECG measurements, such as described in U.S. Pat. No. 8,301,232, it is possible to use a mobile device to measure the pulse at one extremity while simultaneously taking ECG measurements, and then measure the pulse at another extremity or position while again simultaneously taking ECG measurements. The heart rate signals are then aligned with the ECG signals to determine a time difference or differential PAT. The differential PAT, once calibrated to the individual, can be used to estimate and track blood pressure.

Figure 8:
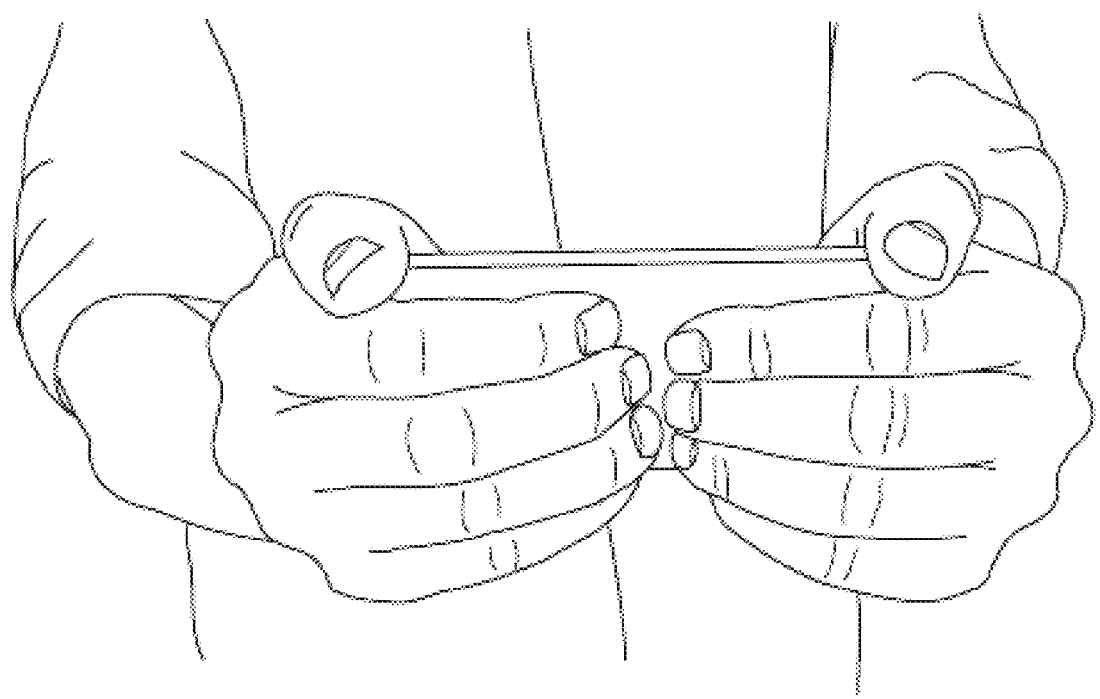
FIG. 8 shows a rear view of a device with electrodes attached which can implement the methods of this disclosure.

For example, a person can place their left and right hands on the electrodes of a mobile phone back cover or protective case configured to measure and record ECG measurements, as shown in FIG. 8, while simultaneously placing a finger over the back camera lens on the mobile device. Software then calculates a PAT from the initiation of the QRS complex to the sensing of blood flow at the finger using the camera of the mobile device as a PPG. These steps can be repeated using a different location of the body such as a finger from the other hand or foot. Software downloadable to the mobile device averages the two QRS signals from the ECG, and time-aligns the two PPG measurements with the averaged ECG to calculate the differential PAT. As described above, software downloadable to the mobile phone can correlate the differential PAT to blood pressure. The correlation merely requires calibration after using a standard blood pressure measurement and consistent use of the same extremities for measuring heart rate.

While preferred embodiments of the presently described subject matter have been shown and described herein, it will be obvious to those skilled in the art that such embodiments are provided by way of example only. Numerous variations, changes, and substitutions will now occur to those skilled in the art without departing from the subject matter described herein. It should be understood that various alternatives to the embodiments of the subject matter described herein may be employed in practicing the subject matter described here. It is intended that the following claims define the scope of the subject matter described herein and that methods and structures within the scope of these claims and their equivalents be covered thereby.

What is claimed is:

1. A method for non-invasive determination of a blood pressure of a subject, comprising:
   sensing, with an electrocardiogram (ECG) sensor operatively coupled to a mobile computing device, an ECG of the subject;
   sensing, with a first optical sensor operatively coupled to the mobile computing device, concurrently with the ECG sensing, a first photoplethysmogram (PPG) of the subject at a first location on the subject, wherein a distance between a heart of the subject and the first location corresponds to a first distance;
   determining, from the first PPG and the ECG, a first pulse arrival time (PAT) corresponding to the first location;
   sensing, with a second optical sensor operatively coupled to the mobile computing device, concurrently with the ECG sensing, a second PPG of the subject at a second location on the subject, wherein a distance between the heart of the subject and the second location corresponds to a second distance;
   determining, from the second PPG and the ECG, a second pulse arrival time (PAT) corresponding to the second location;
   determining a third distance as a difference between the first distance and the second distance;
   determining a pulse wave velocity (PWV) by dividing the third distance by a differential PAT of the first PAT corresponding to the first location and the second PAT corresponding to the second location; and
   determining, by a processing device of the mobile computing device, the blood pressure of the subject from the PWV.

2. The method of claim 1, further comprising:
   determining the blood pressure a plurality of times in accordance with claim 1;
   sensing, at the first location, with the first optical sensor, a PPG at a time t after the plurality of times ($PPG_A^t$);
   determining, from $PPG_A^t$, a PAT corresponding to the first location at the time t ($PAT_A^t$);
   sensing, at the second location, with the second optical sensor, a PPG at the time t ($PPG_B^t$);
   determining, from $PPG_B^t$, a PAT corresponding to the second location at the time t ($PAT_B^t$);
   determining a PAT differential at the time t from the $PAT_A^t$ and the $PAT_B^t$; and
   determining the blood pressure of the subject at the time t based on the relationship that the blood pressure is inversely proportional to the PAT differential.

3. The method of claim 1, wherein the first and the second optical sensors each comprise a camera that operates at a minimum speed of 30 frames per second.

4. The method of claim 1, wherein the mobile computing device comprises first and second electrodes of the ECG sensor, the first optical sensor, and the second optical sensor.

5. The method of claim 4, wherein the first and second electrodes are removable from the mobile computing device.

6. The method of claim 1, further comprising providing the blood pressure of the subject to be displayed on the mobile computing device.

7. The method of claim 1, further comprising providing the blood pressure of the subject to be displayed on a device in communication with the mobile computing device.

8. The method of claim 1, wherein the mobile computing device comprises one of: a smart watch, a wristlet, a smart phone, or a tablet.

9. A smartwatch or a wristlet, comprising:
   a processor;
   an electrocardiogram (ECG) sensor configured to sense electrical signals of a heart, wherein the ECG sensor comprises a first electrode and a second electrode, the ECG sensor coupled to the processor;
   a first optical sensor and a second optical sensor, the first and second optical sensors operatively coupled to the processor;
   a non-transitory computer readable storage medium encoded with a computer program including instructions executable by the processor to cause the processor to:
   sense, with the ECG sensor, an ECG of the subject;
   sense, with the first optical sensor, concurrently with the ECG sensing, a first photoplethysmogram (PPG)

of the subject at a first location on the subject, wherein a distance between a heart of the subject and the first location corresponds to a first distance;

determine, from the first PPG and the ECG, a first pulse arrival time (PAT) corresponding to the first location;

sense, with the second optical sensor, concurrently with the ECG sensing, a second PPG of the subject at a second location on the subject, wherein a distance between the heart of the subject and the second location corresponds to a second distance;

determine, from the second PPG and the ECG, a second pulse arrival time (PAT) corresponding to the second location;

determine a third distance as a difference between the first distance and the second distance;

determine a pulse wave velocity (PWV) by dividing the third distance by the differential PAT of the first PAT corresponding to the first location and the second PAT corresponding to the second location; and determine the blood pressure of the subject from the PWV.

10. The smartwatch or the wristlet of claim 9, the processor further to:

determine the blood pressure a plurality of times in accordance with claim 9;

sense, at the first location, with the first optical sensor, a PPG at a time t after the plurality of times ($PPG_A^t$);

determine, from $PPG_A^t$, a PAT corresponding to the first location at the time t ($PAT_A^t$);

sense, at the second location, with the second optical sensor, a PPG at the time t ($PPG_B^t$);

determine, from $PPG_B^t$ a PAT corresponding to the second location at the time t ($PAT_B^t$);

determine a PAT differential at the time t from $PAT_A^t$ and $PAT_B^t$; and determine the blood pressure of the subject at the time t based on the relationship that the blood pressure is inversely proportional to the PAT differential.

11. The smartwatch or the wristlet of claim 9, wherein the first and the second optical sensors each comprise a camera that operates at a minimum speed of 30 frames per second.

12. The smartwatch or the wristlet of claim 9, wherein the first and the second electrodes are removable from the smartwatch or wristlet.

13. The smartwatch or the wristlet of claim 9, the processor further to provide the blood pressure of the subject to be displayed on the smartwatch or the wristlet.

14. The smartwatch or the wristlet of claim 9, the processor further to provide the blood pressure of the subject to be displayed on a device in communication with the smartwatch or the wristlet.

15. A non-transitory computer-readable storage medium including instructions that, when executed by a processing device, cause the processing device to:

sense, with an electrocardiogram (ECG) sensor operatively coupled to a mobile computing device, an ECG of the subject;

sense, with a first optical sensor operatively coupled to the mobile computing device, concurrently with the ECG sensing, a first photoplethysmogram (PPG) of the subject at a first location on the subject, wherein a distance between a heart of the subject and the first location corresponds to a first distance;

determine, from the first PPG and the ECG, a first pulse arrival time (PAT) corresponding to the first location;

sense, with a second optical sensor operatively coupled to the mobile computing device, concurrently with the ECG sensing, a second PPG of the subject at a second location on the subject, wherein a distance between the heart of the subject and the second location corresponds to a second distance;

determine, from the second PPG and the ECG, a second pulse arrival time (PAT) corresponding to the second location;

determine a third distance as a difference between the first distance and the second distance;

determine a pulse wave velocity (PWV) by dividing the third distance by the differential PAT of the first PAT corresponding to the first location and the second PAT corresponding to the second location; and determine, by a processing device of the mobile computing device, the blood pressure of the subject from the PWV.

16. The non-transitory computer-readable storage medium of claim 15, the processor further to:

determine the blood pressure a plurality of times in accordance with claim 15;

sense, at the first location, with the first optical sensor, a PPG at a time t after the plurality of times ($PPG_A^t$);

determine, from $PPG_A^t$, a PAT corresponding to the first location at the time t ($PAT_A^t$);

sense, at the second location, with the second optical sensor, a PPG at the time t ($PPG_B^t$);

determine, from $PPG_B^t$, a PAT corresponding to the second location at the time t ($PAT_B^t$);

determine a PAT differential at the time t from $PAT_A^t$ and $PAT_B^t$; and determine the blood pressure of the subject at the time t based on the relationship that the blood pressure is inversely proportional to the PAT differential.

17. The non-transitory computer-readable storage medium of claim 15, wherein the first and the second optical sensors each comprise a camera that operates at a minimum speed of 30 frames per second.

18. The non-transitory computer-readable storage medium of claim 15, wherein the mobile computing device comprises first and second electrodes of the ECG sensor, the first optical sensor, and the second optical sensor.

19. The non-transitory computer-readable storage medium of claim 18, wherein the first and the second electrodes are removable from the mobile computing device.

20. The non-transitory computer-readable storage medium of claim 15, the processor further to provide the blood pressure of the subject to be displayed on the mobile computing device.

21. The non-transitory computer-readable storage medium of claim 15, the processor further to provide the blood pressure of the subject to be displayed on a device in communication with the mobile computing device.

22. The non-transitory computer-readable storage medium of claim 15, wherein the mobile computing device comprises one of: a smart watch, a wristlet, a smart phone, or a tablet.

* * * * *